United States Patent
Levin et al.

(10) Patent No.: US 11,116,563 B2
(45) Date of Patent: Sep. 14, 2021

(54) MULTI-CHANNEL RF ABLATION

(71) Applicant: Biosense Webster (Israel) Ltd., Yokneam (IL)

(72) Inventors: Michael Levin, Haifa (IL); Boris Ashkinezer, Akko (IL); Eyal Rotman, Kiriat Tivon (IL); Shlomo Fried, Zichron yaakov (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 477 days.

(21) Appl. No.: 15/898,052

(22) Filed: Feb. 15, 2018

(65) Prior Publication Data

US 2019/0247108 A1     Aug. 15, 2019

(51) Int. Cl.
| | |
|---|---|
| *A61B 18/12* | (2006.01) |
| *A61B 18/14* | (2006.01) |
| *A61B 18/00* | (2006.01) |

(52) U.S. Cl.
CPC ...... *A61B 18/1206* (2013.01); *A61B 18/1492* (2013.01); *A61B 2018/00351* (2013.01); *A61B 2018/00577* (2013.01); *A61B 2018/00702* (2013.01); *A61B 2018/00732* (2013.01); *A61B 2018/00767* (2013.01);
(Continued)

(58) Field of Classification Search
CPC ........... A61B 2018/00732; A61B 2018/00767; A61B 2018/00827; A61B 2018/00892; A61B 18/1206
See application file for complete search history.

(56) References Cited

U.S. PATENT DOCUMENTS 5,542,916 A * 8/1996 Hirsch ............... A61B 18/1815
604/22
5,837,001 A * 11/1998 Mackey ................. A61B 18/12
607/102

(Continued)

FOREIGN PATENT DOCUMENTS

EP     1 112 720 A1     7/2001

OTHER PUBLICATIONS

International Search Report dated May 2, 2019, International Application No. PCT/IB2019/050928.

*Primary Examiner* — Michael F Peffley
*Assistant Examiner* — Tigist S Demie

(57) ABSTRACT

A plurality of control-signal generators are configured to generate respective control signals having respective control-signal amplitudes and different respective control-signal frequencies, and a plurality of signal adders are configured to produce respective composite signals for application to a subject, by adding the control signals to respective ablation signals having respective ablation-signal amplitudes. The control-signal generators are configured to generate the control signals such that respective ratios between the control-signal amplitudes and the ablation-signal amplitudes are constant during the application of the composite signals to the subject. A plurality of controlled voltage dividers are configured to adjust respective amplitudes of the composite signals during the application of the composite signals to the subject, and one or more controllers are configured to control the adjusting of the amplitudes by the controlled voltage dividers, in response to respective currents of, and respective voltages of, the control signals, and based on the constant ratios.

10 Claims, 3 Drawing Sheets

(52) U.S. Cl.
CPC .............. *A61B 2018/00791* (2013.01); *A61B 2018/00827* (2013.01); *A61B 2018/00875* (2013.01); *A61B 2018/00892* (2013.01); *A61B 2018/128* (2013.01); *A61B 2018/1273* (2013.01)

(56) References Cited

U.S. PATENT DOCUMENTS

| | | |
|---|---|---|
| 9,005,193 B2 | 4/2015 | Govari et al. |
| 2004/0006337 A1 | 1/2004 | Nasab et al. |
| 2007/0255269 A1 | 11/2007 | Shin |
| 2009/0062786 A1 | 3/2009 | Garito et al. |
| 2012/0116386 A1 | 5/2012 | Govari et al. |
| 2012/0116387 A1* | 5/2012 | Govari ............... A61B 18/1206 606/41 |
| 2014/0012253 A1 | 1/2014 | Mathur |

\* cited by examiner

MULTI-CHANNEL RF ABLATION

FIELD OF THE INVENTION

The present invention relates to radiofrequency (RF) ablation, such as for the treatment of cardiac arrhythmias.

BACKGROUND

In a multi-channel ablation procedure, multiple ablation currents are applied, simultaneously, over a plurality of channels.

U.S. Pat. No. 9,005,193 describes an apparatus, including an energy generator, configured to supply first ablation power modulated at a first frequency and second ablation power modulated at a second frequency different from the first frequency. The apparatus also includes a probe, having at least one electrode coupled to receive the first and second ablation powers simultaneously and to dissipate the first and second ablation powers in body tissue in contact with the at least one electrode.

US Patent Application Publication 2012/0116386 describes an apparatus, including a current source that has a transformer having a primary winding coupled to receive input power. The transformer has a secondary winding having a first plurality of secondary taps configured to supply electrical power at an ablation frequency to an electrode in contact with body tissue. The issue has an impedance, and is ablated by the electrical power. The current source has a second plurality of capacitors. The apparatus also includes a controller that is configured to select one of the secondary taps and at least one of the capacitors in response to the impedance and the ablation frequency, and to connect the selected secondary tap to the selected at least one of the capacitors.

SUMMARY OF THE INVENTION

There is provided, in accordance with some embodiments of the present invention, apparatus that includes a plurality of control-signal generators, configured to generate respective control signals having respective control-signal amplitudes and different respective control-signal frequencies. The apparatus further includes a plurality of signal adders, configured to produce respective composite signals for application to a subject, by adding the control signals to respective ablation signals having respective ablation-signal amplitudes, the control-signal generators being configured to generate the control signals such that respective ratios between the control-signal amplitudes and the ablation-signal amplitudes are constant during the application of the composite signals to the subject. The apparatus further includes a plurality of controlled voltage dividers, configured to adjust respective amplitudes of the composite signals during the application of the composite signals to the subject, and one or more controllers, configured to control the adjusting of the amplitudes by the controlled voltage dividers, in response to respective currents of, and respective voltages of, the control signals, and based on the constant ratios.

In some embodiments, the ablation signals have a single common ablation-signal frequency.

In some embodiments, a difference between the ablation-signal frequency and the control-signal frequency that is closest to the ablation-signal frequency, relative to the other control-signal frequencies, is between 500 and 1500 Hz.

In some embodiments, a difference between any pair of successive ones of the control-signal frequencies that are both greater than or both less than the ablation-signal frequency, is between 500 and 1500 Hz.

In some embodiments, the ablation signals have respective ablation-signal frequencies, and a difference between a highest one of the ablation-signal frequencies and a lowest one of the ablation-signal frequencies is less than 500 Hz.

In some embodiments, each of the ratios is less than 1:15.

In some embodiments, each of the ratios is less than 1:80.

In some embodiments, the apparatus further includes a plurality of electrodes, each of which is configured to apply a respective one of the composite signals to the subject.

In some embodiments, the apparatus further includes a processor configured to communicate one or more target parameters to the controllers, the controllers being configured to control the adjusting of the amplitudes of the composite signals by the controlled voltage dividers, in response to the communicated target parameters.

In some embodiments, the target parameters include at least one target power for the ablation signals, and the controllers are configured to control the adjusting of the amplitudes of the composite signals by the controlled voltage dividers by:

calculating respective powers of the ablation signals, based on the respective currents of, and respective voltages of, the control signals, and based on the constant ratios, comparing the calculated powers to the target power, and in response to the comparing, controlling the adjusting of the amplitudes of the composite signals by the controlled voltage dividers.

There is further provided, in accordance with some embodiments of the present invention, a method that includes generating a plurality of control signals having respective control-signal amplitudes and different respective control-signal frequencies. The method further includes producing a plurality of composite signals for application to a subject, by adding the control signals to respective ablation signals having respective ablation-signal amplitudes, respective ratios between the control-signal amplitudes and the ablation-signal amplitudes being constant during the application of the composite signals to the subject. The method further includes controlling respective amplitudes of the composite signals during the application of the composite signals to the subject, in response to respective currents of, and respective voltages of, the control signals, and based on the constant ratios.

In some embodiments, the method further includes applying the generated composite signals to the subject, using a plurality of electrodes.

In some embodiments, applying the generated composite signals to the subject includes applying the generated composite signals to cardiac tissue of the subject.

The present invention will be more fully understood from the following detailed description of embodiments thereof, taken together with the drawings, in which:

DETAILED DESCRIPTION OF EMBODIMENTS

Overview

It may be challenging to perform multi-channel ablation on a subject. On the one hand, if the multiple ablation signals share a common frequency, it may be difficult to separately monitor and control each of the ablation signals, due to cross-talk between the channels. One possible solution is to modulate each of the ablation signals differently. However, such modulation may introduce parasitic frequencies that disturb nearby equipment, such as an electrocardiographic (ECG) monitor. On the other hand, assigning different respective frequencies to the ablation signals may also be problematic, due to the intermodulation distortion that may be introduced.

To address this challenge, embodiments of the present invention use a common RF frequency (and phase) for all of the ablation signals, but add, to the ablation signals, different respective control signals having relatively small amplitudes. The control signals have different respective frequencies that are relatively close to the frequency of the ablation signals, and the amplitude of each control signal is a fixed fraction of the amplitude of the corresponding ablation signal. Due to these properties of the control signals, the ablation signals may be indirectly monitored by, and controlled responsively to, monitoring the control signals. At the same time, due to the relatively small amplitude of the control signals, relatively little intermodulation distortion is introduced.

Advantageously, although each of the control-signal frequencies is close to the ablation-signal frequency, all of the frequencies are sufficiently different from each other such as to inhibit the generation of problematic parasitic frequencies. For example, the difference between any two of the frequencies may be greater than the bandwidth of a typical ECG signal, such that the smallest parasitic frequency that might be generated—which is generally equal to the smallest difference between any two of the frequencies—does not disturb the ECG recording.

System Description

Figure 1:
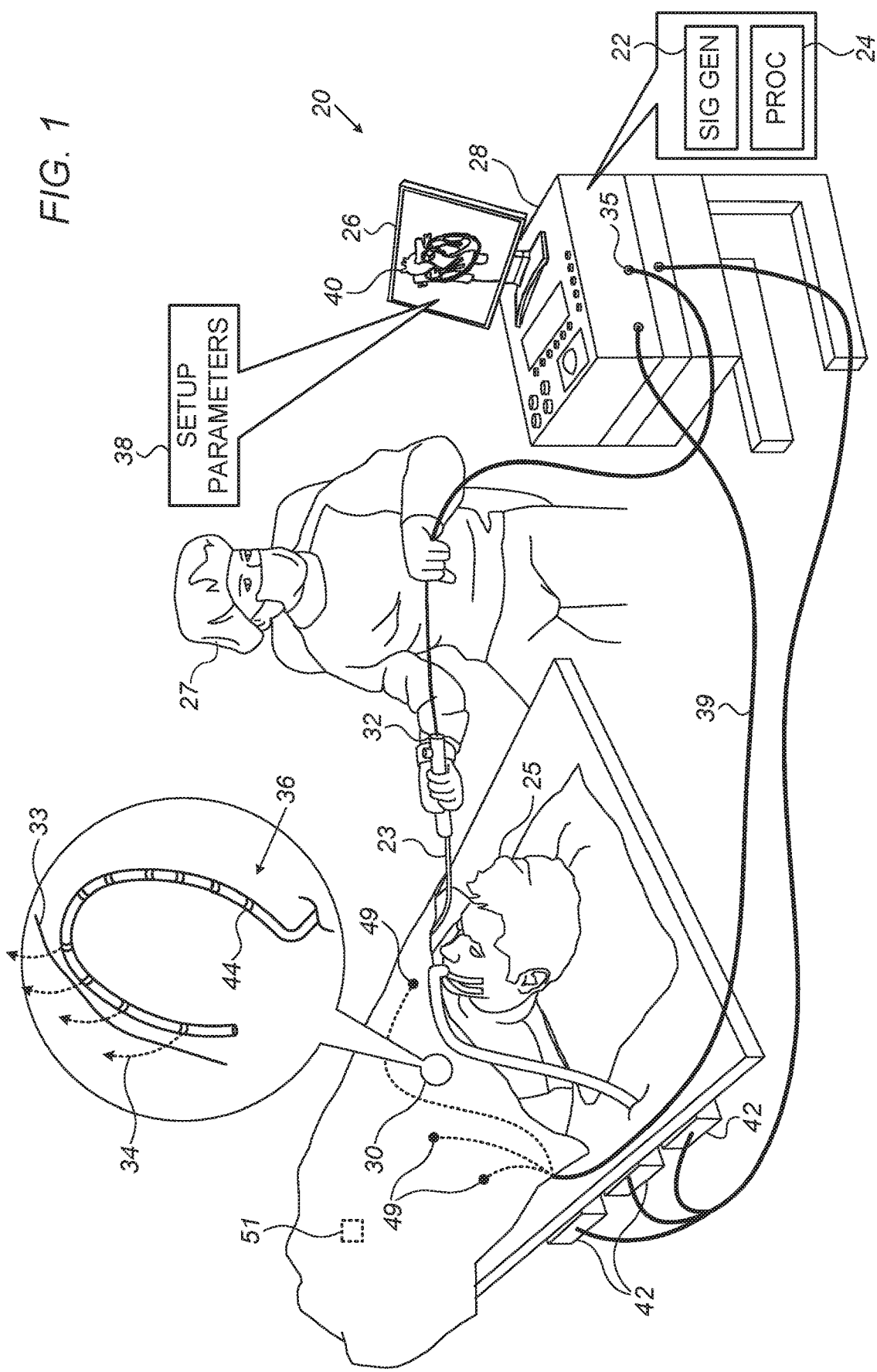
FIG. 1 is a schematic illustration of a system for multi-channel ablation, in accordance with some embodiments of the present invention.

Reference is initially made to FIG. 1, which is a schematic illustration of a system 20 for multi-channel ablation, in accordance with some embodiments of the present invention. FIG. 1 depicts a physician 27 performing a multi-channel cardiac ablation procedure on a subject 25, using an ablation catheter 23 whose distal end 36 comprises a plurality of ablation electrodes 44.

To begin the procedure, physician 27 inserts catheter 23 into the subject, and then navigates the catheter, using a control handle 32, to an appropriate site within, or external to, the heart 30 of subject 25. Subsequently, the physician brings distal end 36 into contact with tissue 33, such as myocardial or epicardial tissue, of heart 30. Next, a signal-generating unit (SIG GEN) 22 generates a plurality of signals 34, which are referred to herein as "composite signals" or "composite ablation signals," as explained below with reference to FIG. 2. Signals 34 are carried through catheter 23, over different respective channels, to electrodes 44, such that each electrode applies a different respective one of signals 34 to the tissue of the subject.

Typically, the ablation is unipolar, in that signals 34 flow between electrodes 44 and an external electrode, or "return patch" 51, that is coupled externally to the subject, typically to the subject's torso.

System 20 further comprises a processor (PROC) 24. Processor 24 is configured to receive from physician 27 (or any other user), prior to and/or during the ablation procedure, setup parameters 38 for the procedure. For example, using one or more suitable input devices such as a keyboard, mouse, or touch screen, the physician may input, for each ablation signal, a maximum power, a maximum current amplitude, a maximum voltage amplitude, a duration of the signal, and/or any other relevant parameters. (Typically, these parameters are the same across all of the signals.) In response to receiving setup parameters 38, processor 24 communicates the setup parameters to signal-generating unit 22, such that signal-generating unit 22 may generate signals 34 in accordance with the setup parameters. Additionally, the processor may display the setup parameters on a display 26 (which may comprise the aforementioned touch screen).

Processor 24 may be further configured to track the respective positions of electrodes 44 during the procedure, using any suitable tracking technique. For example, distal end 36 may comprise one or more electromagnetic position sensors, which, in the presence of an external magnetic field generated by one or more magnetic-field generators 42, output signals that vary with the positions of the sensors. Based on these signals, the processor may ascertain the positions of the electrodes. Alternatively, for each electrode, processor 24 may ascertain the respective impedances between the electrode and a plurality of external electrodes 49 coupled to subject 25 at various different locations, and then compute the ratios between these impedances, these ratios being indicative of the electrode's location. As yet another alternative, the processor may use both electromagnetic tracking and impedance-based tracking, as described, for example, in U.S. Pat. No. 8,456,182, whose disclosure is incorporated herein by reference.

In some embodiments, the processor ascertains which of electrodes 44 are in contact with the subject's tissue, and causes those electrodes, but not the other electrodes, to deliver signals 34 to the tissue. In other words, the processor may select a subset of channels leading to those electrodes that are in contact with the tissue, and then cause signals 34 to be passed over the selected subset of channels, but not over the other channels.

In some embodiments, the processor displays, on display 26, a relevant image 40 of the subject's anatomy, annotated, for example, to show the current position and orientation of distal end 36. Alternatively or additionally, based on signals received from relevant sensors disposed at distal end 36, the processor may track the temperature and/or impedance of tissue 33, and control signal-generating unit 22 responsively thereto, as further described below with reference to FIG. 2. Alternatively or additionally, the processor may perform any other relevant function for controlling, or otherwise facilitating the performance of, the procedure.

Processor 24, and signal-generating unit 22, typically reside within a console 28. Catheter 23 is connected to console 28 via an electrical interface 35, such as a port or socket. Signals 34 are thus carried to distal end 36 via interface 35. Similarly, signals for tracking the position of distal end 36, and/or signals for tracking the temperature and/or impedance of the tissue, may be received by processor 24 via interface 35.

Typically, the functionality of processor 24, as described herein, is implemented at least partly in software. For example, processor 24 may comprise a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Notwithstanding the particular type of ablation procedure illustrated in FIG. 1, it is noted that the embodiments described herein may be applied to any suitable type of multi-channel ablation procedure.

Generating and Controlling the Composite Ablation Signals

Figure 2:
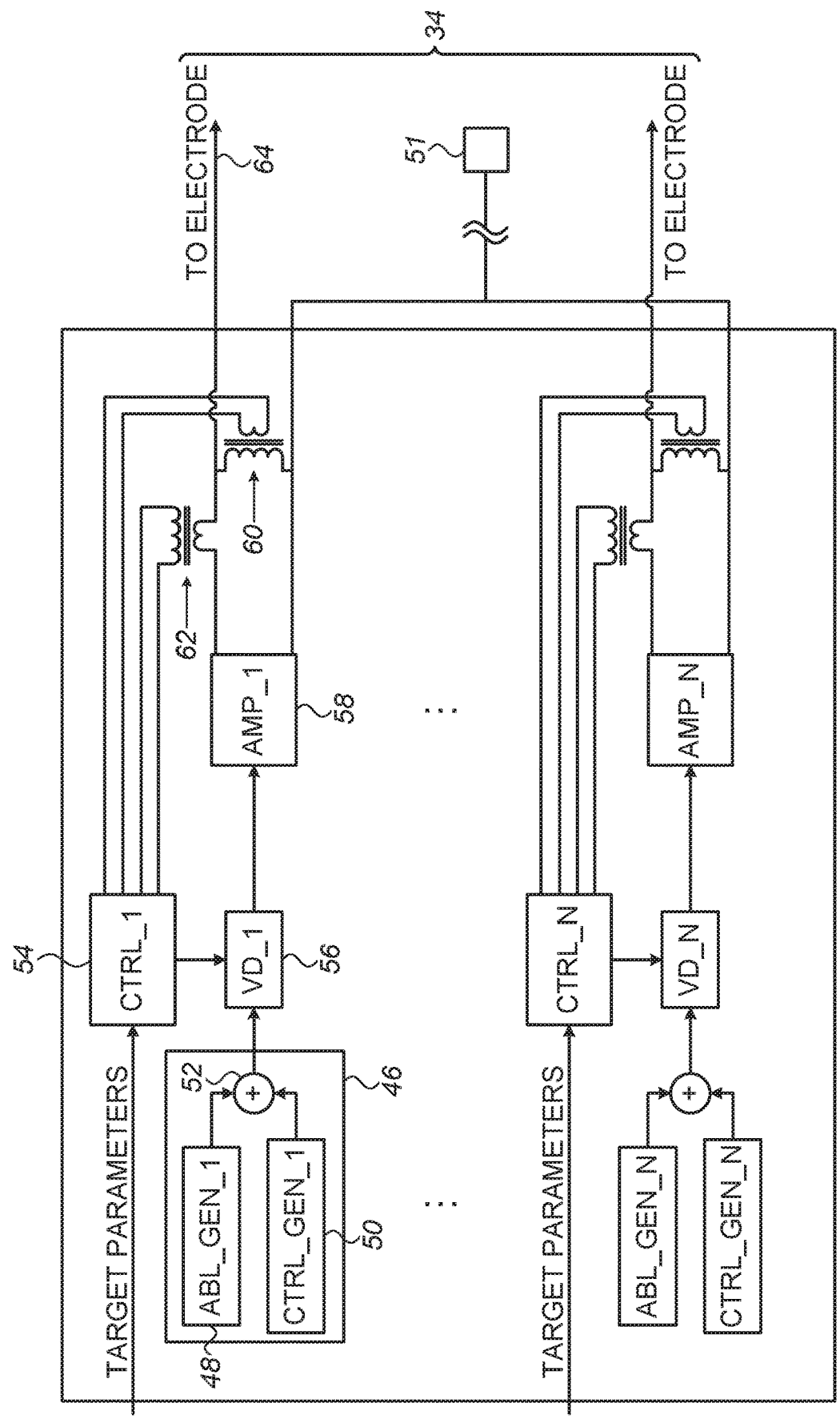
FIG. 2 is a schematic illustration of a signal-generating unit, in accordance with some embodiments of the present invention.

Reference is now made to FIG. 2, which is a schematic illustration of signal-generating unit 22, in accordance with some embodiments of the present invention.

Signal-generating unit 22 comprises a plurality of signal generators 46, configured to generate signals 34, respectively, for application to subject 25, as described above with reference to FIG. 1. In other words, each signal generator 46 is configured to generate a different respective signal 34 to be passed through the tissue of the subject.

Typically, each signal generator 46 comprises a control-signal generator 50, configured to generate a control signal, an ablation-signal generator 48, configured to generate an ablation signal, and a signal adder 52, configured to produce signal 34 by adding the generated control signal to the generated ablation signal. By virtue of signal 34 being a combination of the control signal and the ablation signal, signal 34 is referred to herein as a "composite signal" or "composite ablation signal," as noted above with reference to FIG. 1. (It is noted that any "signal" described herein may alternatively be referred to as a "current," such that, for example, signals 34 may be referred to as "composite ablation currents.")

While the control signals have different respective control-signal frequencies, the ablation signals typically have a single common ablation-signal frequency (and a single common phase). Alternatively, the ablation-signal frequencies may differ slightly from each other, such that, for example, the difference between the highest ablation-signal frequency and the lowest ablation-signal frequency is less than 500 Hz, which is the typical bandwidth of an ECG signal.

In general, signal-generating unit 22 may comprise any suitable number of signal generators 46, corresponding to the number of ablation electrodes 44. For example, signal-generating unit 22 may comprise 2-20 signal generators 46. FIG. 2 schematically illustrates "N" signal generators 46, by showing both the first and $N^{th}$ signal generator. The first ablation-signal generator 48 is indicated by the notation "ABL_GEN_1," while the $N^{th}$ ablation-signal generator 48 is indicated by the notation "ABL_GEN_N." Similarly, the first control-signal generator 50 is indicated by the notation "CTRL_GEN_1," while the $N^{th}$ control-signal generator 50 is indicated by the notation "CTRL_GEN_N."

In other embodiments, signal generators 46 comprise respective control-signal generators and signal adders, but do not comprise respective ablation-signal generators. Rather, signal-generating unit 22 comprises a single ablation-signal generator, which supplies an ablation signal to each signal adder. In the context of the present application, including the claims, such an ablation signal may be referred to as a "plurality of ablation signals," given that the ablation signal is passed, over multiple lines, to multiple signal adders.

Each ablation-signal generator 48 and control-signal generator 50 may comprise a digital-to-analog converter, a stable analog free-running generator, or a direct digital synthesizer (DDS), such as the AD9854 DDS by Analog Devices, Inc. of Norwood, Mass., USA.

Typically, the smallest difference between any two of the control-signal frequencies is large enough such as to inhibit the generation of problematic parasitic frequencies. For example, this difference may be greater than 500 Hz, which is the typical bandwidth of an ECG signal. Similarly, the difference between the ablation-signal frequency and the closest control-signal frequency (i.e., the control-signal frequency that is closest to the ablation-signal frequency, relative to the other control-signal frequencies) is typically greater than 500 Hz. (For embodiments in which there are multiple ablation-signal frequencies, the smallest difference between any one of the ablation-signal frequencies and any one of the control-signal frequencies may be greater than 500 Hz.) Nevertheless, the control-signal frequencies are typically close enough to the ablation-signal frequency such that the control signals and ablation signals have similar frequency-related effects on the tissue of subject 25.

For example, the difference between any pair of successive frequencies may be between 500 and 1500 Hz. In other words, (i) the difference between the ablation-signal frequency and the closest control-signal frequency, and (ii) the difference between any pair of successive control-signal frequencies that are both greater than or both less than the ablation-signal frequency, may be between 500 and 1500 Hz. (Two given frequencies are said to be "successive" if, when all of the frequencies are listed in order of increasing or decreasing magnitude, the two given frequencies are listed sequentially.) Thus, for example, given a difference of 1 kHz, an ablation-signal frequency of 486 kHz, and N channels (assuming, for simplicity, that N is even), the control-signal frequencies may consist of 486–N/2 kHz, 486–N/2+1 kHz, ... 485 kHz, 487 kHz, ... 486+N/2–1 kHz, and 486+N/2 kHz.

Each control-signal generator is configured to generate its control signal such that the ratio between the amplitude of the control signal and the amplitude of the ablation signal to which the control signal is added is constant (or "fixed") during the application of the composite signal. As further described below, the constancy of this ratio may facilitate controlling the composite signal. Typically, the ratio is less than 1:15, such as less than 1:20, 1:40, 1:60, 1:80, 1:100, or 1:120, such that, by virtue of the relatively small amplitude of the control signal, relatively little intermodulation distortion is introduced. For example, if, following the amplification of the composite signal as described below, the ablation signal has an amplitude of 90-110 V, the control signal may have an amplitude of 1-2 V. Due to the frequency of the control signal being similar to that of the ablation signal, the two signals see a similar impedance across the tissue of the subject, such that the ratio between the voltages of the two signals is generally the same as the ratio between the currents of the two signals.

Signal-generating unit 22 further comprises a plurality of controlled voltage dividers 56, configured to adjust the respective amplitudes of the composite signals during the application of the composite signals to the subject. Typically, signal-generating unit 22 comprises one controlled voltage divider 56 for each signal generator 46, such that the output from each signal adder 52 is passed to a different respective controlled voltage divider. FIG. 2 indicates the first controlled voltage divider by the notation "VD 1," and the $N^{th}$ controlled voltage divider by the notation "VD N." Each controlled voltage divider may comprise, for example, a digital potentiometer, such as the AD5122 digital potentiometer by Analog Devices.

Typically, signal-generating unit 22 further comprises a plurality of amplifiers 58, configured to amplify the adjusted signals received from the controlled voltage dividers. In FIG. 2, the first amplifier 58 is indicated by the notation "AMP_1," while the $N^{th}$ amplifier is indicated by the notation "AMP_N." The amplified signals are output to electrodes 44, over a plurality of channels 64.

Signal-generating unit 22 further comprises one or more controllers 54, configured to control the adjusting of the amplitudes by controlled voltage dividers 56, in response to the respective currents of, and respective voltages of, the control signals, and based on the respective constant ratios between the control-signal amplitudes and ablation-signal amplitudes. Typically, signal-generating unit 22 comprises one controller 54 for each controlled voltage divider 56 (and for each signal generator 46), such that the controlling output from each controller is passed to a different respective controlled voltage divider. FIG. 2 indicates the first controller by the notation "CTRL_1," and the $N^{th}$ controller by the notation "CTRL_N." Typically, each controller comprises an analog front-end, an analog-to-digital converter, a digital filter, and a processor. Some or all of these components may be included in a field-programmable gate array (FPGA), such as a Cyclone Family FPGA by Intel of Santa Clara, Calif., USA.

Signal-generating unit 22 further comprises, for each channel 64, circuitry, such as a voltage transformer 60 and a current transformer 62, configured to step-down the voltage and current of signal 34 to measurable levels. The stepped-down voltage (e.g., the voltage induced across each voltage transformer 60) and the stepped-down current (e.g., the current induced through each current transformer 62) are input to the analog front-end of controller 54, and are then converted, by the analog-to-digital converter, to digital signals. These signals are then filtered, by the digital filter, such that only the control-signal frequency remains. Subsequently, the controller (in particular, the processor of the controller) calculates the voltage and current of the control signal from the filtered signals. For example, the controller may measure the amplitudes of the filtered signals, and then multiply each of these amplitudes by the appropriate transformer ratio, such as to obtain the voltage and current of the control signal.

Next, given the constant ratio between the control signal and the ablation signal, the controller may compute one or more properties of the ablation signal. For example, given a voltage amplitude $V_{CTRL}$ and a current amplitude $I_{CTRL}$ of the control signal, the controller may compute the voltage amplitude $V_{ABL}$ and the current amplitude $I_{ABL}$ of the ablation signal, by dividing each of $V_{CTRL}$ and $I_{CTRL}$ by R, the above-described ratio of the control-signal amplitude to the ablation signal amplitude. For example, if R=1:100, then $V_{ABL}=100*V_{CTRL}$, and $I_{ABL}=100*I_{CTRL}$. Subsequently, the controller may compute the power of the ablation signal from $V_{ABL}$ and $I_{ABL}$.

During the procedure, processor 24 continually communicates target parameters to signal-generating unit 22, and in particular, to controllers 54. These parameters may include setup parameters 38, and/or parameters that are computed responsively to monitoring the subject during the procedure. The target parameters may be communicated directly from processor 24, or via any suitable hardware or other circuitry not shown in FIG. 2. The controller continually compares one or more measured or computed parameters of signal 34 to the target parameters, and, in response thereto, controls the adjusting of the amplitude of signal 34 by the controlled voltage dividers.

For example, the processor may continually (i) monitor the temperature at the interface between distal end 36 and tissue 33, (ii) responsively to this temperature, compute a target ablation-signal power, which does not exceed the maximum power specified by physician 27, and (iii) communicate the target ablation-signal power to the controllers. Each controller may continually compare the received target power to the computed ablation-signal power, and, responsively to this comparison, cause the corresponding controlled voltage divider to increase or decrease the amplitude of signal 34, such as to better match the target ablation-signal power.

In some embodiments, the target parameters include a target power for the composite signals, alternatively or additionally to the aforementioned ablation-signal target power. (In other words, the target parameters may take into account the contribution of the control signals.) In such embodiments, each controller may compute the composite-signal voltage $V_{COMP}$, and the composite-signal current $I_{COMP}$, by multiplying each of $V_{CTRL}$ and $I_{CTRL}$ by (1+1/R). The controller may then compute the power of the composite signal from $V_{COMP}$ and $I_{COMP}$, compare this power to the target, and then control the controller voltage divider responsively thereto.

Typically, a single target power is specified for all of the channels. In some cases, however, different respective target powers may be specified for at least some of the channels.

Alternatively or additionally to comparing the power of the ablation signal or of the composite signal to a target power, the controller may compare the current of the ablation signal or of the composite signal to a target current, and/or the voltage of the ablation signal or of the composite signal to a target voltage, and control the controller voltage divider responsively thereto.

It is noted that, alternatively or additionally to the circuitry described above (such as the signal generators, controlled voltage dividers, and controllers), signal-generating unit 22 may comprise any other suitable circuitry, such as, for example, output transformers for impedance matching, passive bandpass and/or band-stop filters, or passive overvoltage protection devices.

In some embodiments, each controller 54 continually calculates the impedance of tissue 33 from the measured voltages and currents, and communicates the calculated impedances to processor 24. Typically, processor 24 displays these impedances on display 26.

Figure 3:
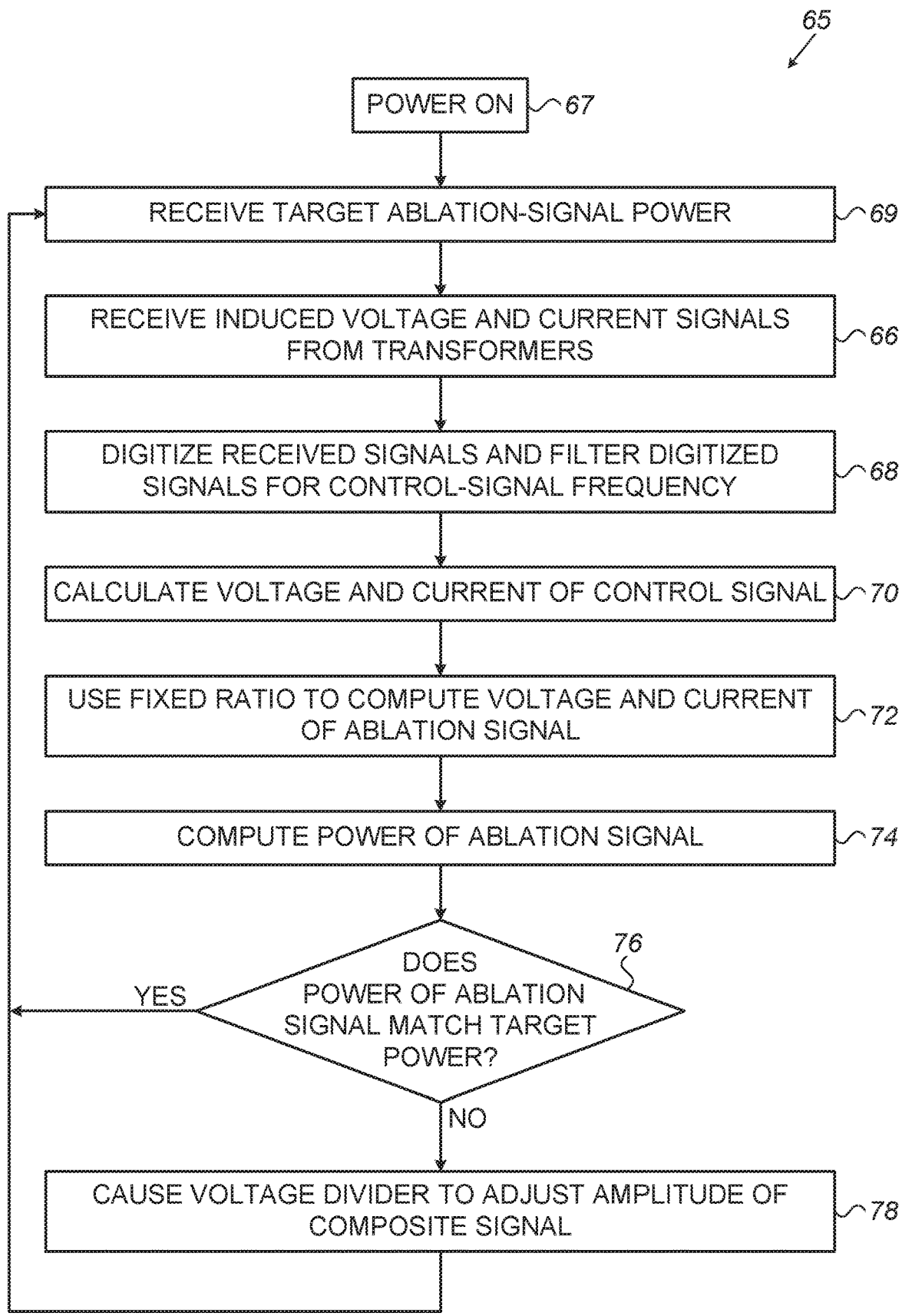
FIG. 3 is a flow diagram for a feedback control loop, in accordance with some embodiments of the present invention.

Reference is now made to FIG. 3, which is a flow diagram for a feedback control loop, in accordance with some embodiments of the present invention.

As described above, each controller 54 effectively implements a feedback control loop, whereby, during the application of the relevant composite signal to the subject, the amplitude of the composite signal is controlled in response to the current and voltage of the control signal that is included in the composite signal. This control loop is more explicitly shown in FIG. 3.

First, prior to the beginning of the control loop, the controller is powered on, at a power-on step 67. Subsequently, the controller receives, from processor 24, a target ablation-signal power, at a target-receiving step 69. Next, at an induced-signal-receiving step 66, the controller receives the induced voltage and current signals from the voltage transformer and the current transformer, respectively. Next, at a digitizing-and-filtering step 68, the controller digitizes the received signals, and then filters the digitized signals for the control-signal frequency, e.g., by applying a bandpass filter to the digitized signals. Subsequently, at a calculating step 70, the controller calculates the voltage and current of the control signal from the filtered signals, as described above with reference to FIG. 2. Next, at a first computing step 72, the controller uses the fixed ratio between the ablation signal and the control signal to compute the voltage and current of the ablation signal.

Subsequently, at a second computing step 74, the controller computes the power of the ablation signal from the voltage and current of the ablation signal. The controller then compares the power of the ablation signal to the target power, at a comparing step 76. If the power matches the target, the controller does not adjust the composite signal, but instead, returns to target-receiving step 69. Otherwise, before returning to target-receiving step 69, the controller causes the controlled voltage divider to adjust the amplitude of the composite signal, at an adjusting step 78.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
   a plurality of control-signal generators, configured to generate respective control signals having respective control-signal amplitudes and different respective control-signal frequencies;
   a plurality of ablation-signal generators configured to generate respective ablation signals;
   a plurality of signal adders, configured to produce respective composite signals for application to a subject, by adding the respective control signals to respective ablation signals having respective ablation-signal amplitudes, the plurality of control-signal generators being configured to generate respective control signals such that respective ratios between the control-signal amplitudes and the ablation-signal amplitudes are constant during the application of the composite signals to the subject;
   a plurality of controlled voltage dividers, configured to adjust respective amplitudes of the composite signals during the application of the composite signals to the subject; and
   one or more controllers, configured to control the adjusting of the respective amplitudes of the composite signals by the plurality of controlled voltage dividers, in response to respective currents of, and respective voltages of, the control signals, and based on the constant ratios.

2. The apparatus according to claim 1, wherein the ablation signals comprise a single common ablation-signal frequency.

3. The apparatus according to claim 2, wherein a difference between the single common ablation-signal frequency and a control-signal frequency of the respective control-signal frequencies that is closest to the ablation-signal frequency, relative to other control-signal frequencies of the respective control-signal frequencies, is between 500 and 1500 Hz.

4. The apparatus according to claim 2, wherein a difference between any pair of successive ones of the control-signal frequencies that are both greater than or both less than the ablation-signal frequency, is between 500 and 1500 Hz.

5. The apparatus according to claim 1, wherein the ablation signals have respective ablation-signal frequencies, and wherein a difference between a highest one of the ablation-signal frequencies and a lowest one of the ablation-signal frequencies is less than 500 Hz.

6. The apparatus according to claim 1, wherein each of the constant ratios is less than 1:15.

7. The apparatus according to claim 6, wherein each of the ratios is less than 1:80.

8. The apparatus according to claim 1, further comprising a plurality of electrodes, each of which is configured to apply a respective one of the composite signals to the subject.

9. The apparatus according to claim 1, further comprising a processor configured to communicate one or more target parameters to the one or more controllers,
   wherein the one or more controllers are configured to control the adjusting of the amplitudes of the composite signals by the plurality of controlled voltage dividers, in response to the communicated target parameters.

10. The apparatus according to claim 9, wherein the communicated target parameters include at least one target power for the ablation signals, and wherein the one or more controllers are configured to control the adjusting of the amplitudes of the composite signals by the plurality of controlled voltage dividers by:
   calculating respective powers of the ablation signals, based on the respective currents of, and the respective voltages of, the control signals, and based on the constant ratios,
   comparing the respective calculated powers to the at least one target power, and
   in response to the comparing, controlling the adjusting of the respective amplitudes of the composite signals by the controlled voltage dividers.

* * * * *